United States Patent
Ergler et al.

(10) Patent No.: US 10,869,641 B2
(45) Date of Patent: Dec. 22, 2020

(54) MANUFACTURING A COLLIMATOR ELEMENT

(71) Applicant: Siemens Healthcare GmbH, Erlangen (DE)

(72) Inventors: Thorsten Ergler, Erlangen (DE); Vojislav Krstic, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/561,206

(22) Filed: Sep. 5, 2019

(65) Prior Publication Data
US 2020/0077966 A1    Mar. 12, 2020

(30) Foreign Application Priority Data
Sep. 11, 2018   (DE) .................. 10 2018 215 376

(51) Int. Cl.
*A61B 6/06*         (2006.01)
*G21K 1/02*         (2006.01)
(Continued)

(52) U.S. Cl.
CPC ............... *A61B 6/06* (2013.01); *A61B 6/032* (2013.01); *A61B 6/4291* (2013.01); *G21K 1/025* (2013.01); *A61B 6/4241* (2013.01)

(58) Field of Classification Search
None
See application file for complete search history.

(56) References Cited

U.S. PATENT DOCUMENTS

| 5,303,282 A | 4/1994 | Kwasnick et al. |
| 5,949,850 A | 9/1999 | Tang |

(Continued)

FOREIGN PATENT DOCUMENTS

| CN | 103845066 A | 6/2014 |
| CN | 107242879 A | 10/2017 |

(Continued)

OTHER PUBLICATIONS

Makarova, O. V. et al. "Development of a freestanding copper antiscatter grid using deep X-ray lithography" Microsystem Technologies, vol. 9, pp. 395-398, 2003, Springer-Verlag // DOI 10.1007/s00542-002-0256-9.

(Continued)

*Primary Examiner* — Thomas R Artman
(74) *Attorney, Agent, or Firm* — Harness, Dickey & Pierce, P.L.C.

(57) ABSTRACT

A method is disclosed for manufacturing a collimator element. The method includes applying a lithographic coating layer. The lithographic coating layer is then exposed using a grid mask. Exposure regions then correspond to a structure of the collimator element. Here, the structure of the collimator element is aligned on a common focus. The lithographic coating layer is then developed to give a pre-structure of the collimator element. Further, an X-ray absorbing layer is applied via cathode sputtering. At least the X-ray absorbing layer is then removed from regions of the pre-structure. A collimator element, a method for manufacturing a scattered-radiation collimator, a scattered-radiation collimator, a radiation detector and a CT device are also disclosed.

21 Claims, 4 Drawing Sheets

(51) Int. Cl.
*A61B 6/00* (2006.01)
*A61B 6/03* (2006.01)

(56) References Cited

U.S. PATENT DOCUMENTS

| | | | |
|---|---|---|---|
| 6,185,278 B1* | 2/2001 | Appleby | G21K 1/025 378/149 |
| 6,980,629 B1 | 12/2005 | Hoheisel et al. | |
| 6,987,836 B2* | 1/2006 | Tang | G21K 1/025 378/147 |
| 7,310,411 B2* | 12/2007 | Tang | G21K 1/025 378/147 |
| 7,922,923 B2* | 4/2011 | Tang | G21K 1/025 216/36 |
| 2003/0026386 A1* | 2/2003 | Tang | G21K 1/025 378/154 |
| 2006/0072704 A1* | 4/2006 | Tang | G21K 1/025 378/154 |
| 2008/0088059 A1* | 4/2008 | Tang | G21K 1/025 264/261 |
| 2015/0061062 A1* | 3/2015 | Lin | H01L 27/14685 257/432 |
| 2015/0270413 A1 | 9/2015 | Zhang et al. | |
| 2020/0077966 A1* | 3/2020 | Ergler | A61B 6/032 |
| 2020/0268330 A1* | 8/2020 | Altunbas | A61B 6/4283 |

FOREIGN PATENT DOCUMENTS

| | | |
|---|---|---|
| DE | 10241424 A1 | 3/2004 |
| JP | 2004146158 A | 5/2004 |

OTHER PUBLICATIONS

Fischer, Kevin et al. "Fabrication of 2D x-ray antiscatter grids for mammography" Proceedings of SPIE, Proceedings vol. 4145, Advances in X-Ray Optics, pp. 227-234, (2001) // https://doi.org/10.1117/12.411642.

German Office Action for German Patent Application No. DE 102018215376.0 dated Apr. 26, 2019.

* cited by examiner

MANUFACTURING A COLLIMATOR ELEMENT

PRIORITY STATEMENT

The present application hereby claims priority under 35 U.S.C. § 119 to German patent application number DE 102018215376.0 filed Sep. 11, 2018, the entire contents of each of which are hereby incorporated herein by reference.

FIELD

Embodiments of the invention generally relate to a method for manufacturing a collimator element and to a collimator element of this kind, a method for manufacturing a scattered-radiation collimator, a scattered-radiation collimator of this kind and the use thereof, a radiation detector, and a CT device.

BACKGROUND

During the transmission of X-ray or gamma radiation, also called "radiation" below for short, through an object that is to be investigated by way of the radiation, scattered radiation is known to be produced as a result of the interaction of the radiation with the object. In the case of investigations such as X-ray computed tomography, this scattered radiation is undesirable, since it results in artifacts in images that are reconstructed from captured attenuation values.

For the purpose of suppressing this undesired scattered radiation, for radiation detectors in transmission tomographic devices such as X-ray computed tomography devices there are used so-called scattered-radiation collimators or anti-scatter grids (ASGs) that are connected upstream of the radiation detector in the direction of incidence of the radiation. In the case of X-ray computed tomography devices having an X-ray source and a radiation detector for detecting X-rays generated by the X-ray source, a scattered-radiation collimator of this kind typically comprises a plurality of collimator elements that are preferably aligned on the focus of the X-ray source.

Currently, two types of radiation detectors can be differentiated: direct-conversion detectors, and indirect-conversion detectors, the latter also designated optical-conversion detectors below. In the case of direct-conversion detectors, incident radiation, for example X-ray or gamma radiation, is converted directly into electrical voltage signals. In the case of optical-conversion radiation detectors, by contrast, so-called scintillators are used to convert the radiation that is to be detected first into a radiation in the frequency range of (usually visible) light. Downstream light detector arrangements detect these photons and from these, in turn, generate electrical voltage signals.

The individual radiation detector modules—whether of the direct or indirect conversion type—are formed by being separated from one another out of an integral detector material. In practice, hitherto the associated collimator elements have frequently been formed by metal plates that project perpendicularly between the pixels from the radiation entry face of the radiation detector modules, so-called collimator plates.

The collimator elements serve to effectively intercept scattered radiation that is incident at an angle, and to allow substantially only radiation that is incident as far as possible in the principal direction of the radiation to enter the radiation detector module. Below, there may be regarded as the principal direction of the radiation to be detected the direction of propagation of radiation in which, to a substantial extent, the radiation to be detected falls on the radiation detector, which may for example be defined by the collimator elements. Usually here, it is ensured that the radiation to be detected falls from a radiation source substantially perpendicularly on the radiation entry face, that is to say that the principal direction is perpendicular to the radiation entry face. Here, the term "substantially perpendicular" should in each case be understood to mean that the respective directions are perpendicular to one another within certain tolerances, that is to say for example deviations in the wall positions or alignment on the focus.

Suppression of the scattered radiation via the collimators is performed from the direction of radiation behind the patient. That is to say that, as well as the scattered radiation, the collimators also suppress radiation that falls directly/perpendicularly on the detector. This portion of the radiation corresponds to a dosage loss. To put it another way, the collimator element reduces the effective detector surface area (geometric DQE). The objective should therefore be to make the collimator walls as thin as possible but still thick enough to effectively suppress the scattered radiation that falls "non-perpendicularly". Because the absorption of radiation in a material is exponential in relation to its thickness (Beer-Lambert Law), there is a lower limit for the thickness of the walls before they become virtually transparent.

Previous manufacturing methods for 3D ASGs are limited in respect of their minimum wall thickness (e.g. construction from metal plates, selective laser melting (SLM)). Another constraint is that the proportion of tungsten in methods known in the prior art is in some cases only approximately 50% of the volume. The objective should thus be to manufacture thinner walls with better X-ray absorption properties.

Nowadays, the demands for precision in the manufacture and positioning of the collimator elements on the radiation detector are considerable. At the same time, these demands can be expected to increase even further in the future, with the result that it will no longer be possible, or only with great difficulty—that is to say with high production and breakdown costs—to meet the tolerances using previous technologies.

Medical imaging has constantly to be improved. In this context, for example in the area of UHR-CT (ultra-high resolution computed tomography), as pixel size becomes smaller the demands on quality and/or size of the focus increase, as in particular do those on the screening of scattered radiation and manufacturing tolerances in general. The reduction of tolerances in the manufacture, positioning and alignment of collimator elements is primarily connected with the general tendency toward smaller pixels in the z and φ directions. These are the directions that approximately form a plane aligned substantially perpendicular to the principal direction of the radiation to be detected. With a circular or partly circular detector that rotates about an axis of rotational symmetry and in some cases revolves on an orbit path, in an imaging system such as a CT, PET or SPECT detector, the z and φ directions are defined as the direction of insertion (z direction) parallel to the axis of rotational symmetry and the axis of rotation (p direction). As a result of making the pixels smaller in one or both of these directions, a higher resolution of radiation detectors, both temporally and spatially, can be achieved. The smaller the pixels, however, the more precisely must they and the collimator elements be manufactured and arranged, in terms both of between the pixels and between the collimator elements, and of the two in relation to one another.

In this respect, previous grid structures are in the order of magnitude of around 1 mm² with wall thicknesses of somewhat more than 100 μm.

Although an alignment of grid walls in a collimation element is already known from the art, it must be further improved in respect of its tolerances (in relation for example to the possibility, which must be avoided, of the grid walls standing at an angle) and manufacturing costs.

SUMMARY

At least one embodiment of the present invention enables scattered-radiation collimation with an improved dosage efficiency.

Embodiments of the invention include: methods for manufacturing a collimator element, a collimator element, a method for manufacturing a scattered-radiation collimator, a scattered-radiation collimator, a radiation detector, and a CT device.

A method of at least one embodiment, for manufacturing a collimator element, includes at least: in one step, a lithographic coating layer which is at least 0.5 mm thick is applied. In a further step, the lithographic coating layer is exposed in exposure regions that correspond to a structure of the collimator element. Here, the structure of the collimator element is aligned on a common focus. Then, the lithographic coating layer is developed to give a pre-structure of a collimator element. In a still further step, an X-ray absorbing layer is applied via cathode sputtering. In a further step, at least the X-ray absorbing layer is removed from regions of the pre-structure.

A collimator element is manufactured by a method according to at least one embodiment of the invention.

A method of at least one embodiment, for manufacturing a scattered-radiation collimator, includes at least the following. In one step, a number of collimator elements according to the invention are provided. In a further step, the collimator elements are joined together to form a scattered-radiation collimator. Here, "a number" means one or more. In principle, it would therefore be possible within the context of the invention to make a scattered-radiation collimator having only one collimator element. Because of the shape, in the manner of a circle chord, of the radiation detectors in CT devices, however, it is frequently more favorable and simpler to make the scattered-radiation collimator out of a plurality of collimator elements. When these are joined together, preferably each collimator element is aligned on the focus. Joining together may for example be performed form-fittingly and/or force-fittingly and/or via gluing, welding, soldering or similar types of connection. The scattered-radiation collimator mentioned in the introduction accordingly includes a number of collimator elements according to the invention and is manufactured in particular according to the method according to the invention that is described above.

The radiation detector of at least one embodiment includes a scattered-radiation collimator according to at least one embodiment of the invention. The radiation detector may take the form of a CT, PET or SPECT detector. In particular, it is a photon-counting and where appropriate also energy-resolved X-ray detector. In this case, a grid shaft is associated with each pixel of the radiation detector. That is to say that the grid shaft is positioned in relation to the pixel such that direct (not scattered) radiation falls on the pixel through the grid shaft.

The radiation detector of at least one embodiment includes a scattered-radiation collimator according to at least one embodiment of the invention. The radiation detector may take the form of a CT, PET or SPECT detector. In particular, it is a photon-counting and where appropriate also energy-resolved X-ray detector. In this case, a grid shaft is associated with each pixel of the radiation detector. That is to say that the grid shaft is positioned in relation to the pixel such that direct (not scattered) radiation falls on the pixel through the grid shaft.

The radiation detector that is described above may in principle be a constituent part of any desired X-ray device, such as a radiography device, an angiography device or in particular a CT device. The CT device of at least one embodiment includes a radiation detector according to at least one embodiment of the invention. The fundamental functioning of a radiation detector and of a CT device is known to those skilled in the art, so no further explanations in this regard will be given here.

New radiation detectors and/or CT devices already having the collimator elements and/or scattered-radiation collimators according to at least one embodiment of the invention may thus be made. Advantageously, however, already existing radiation detectors or CT devices may be retrofitted with the collimator elements according to at least one embodiment of the invention and/or scattered-radiation collimators according to at least one embodiment of the invention.

A scattered-radiation collimator according to at least one embodiment of the invention is used to absorb scattered radiation before the scattered radiation falls on a radiation detector.

A method according to at least one embodiment of the invention, for manufacturing a collimator element, comprises:

applying a lithographic coating layer;

exposing the lithographic coating layer in exposure regions corresponding to a structure of the collimator element, the structure of the collimator element being aligned on a common focus;

developing the lithographic coating layer to provide a pre-structure of the collimator element;

applying an X-ray absorbing layer via cathode sputtering; and removing at least the X-ray absorbing layer from regions of the pre-structure.

A collimator element according to at least one embodiment of the invention, is manufactured by at least applying a lithographic coating layer;

exposing the lithographic coating layer in exposure regions corresponding to a structure of the collimator element, the structure of the collimator element being aligned on a common focus;

developing the lithographic coating layer to provide a pre-structure of the collimator element;

applying an X-ray absorbing layer via cathode sputtering; and removing at least the X-ray absorbing layer from regions of the pre-structure.

A method according to at least one embodiment of the invention, for manufacturing a scattered-radiation collimator, comprises:

providing a number of collimator elements, each of the collimator elements being manufactured by at least applying a lithographic coating layer, exposing the lithographic coating layer in exposure regions corresponding to a structure of the collimator element, the structure of the collimator element being aligned on a common focus, developing the lithographic coating layer to provide a pre-structure of the collimator element;

applying an X-ray absorbing layer via cathode sputtering, and removing at least the X-ray absorbing layer from regions of the pre-structure; and joining the number of collimator elements together, to form the scattered-radiation collimator.

A scattered-radiation collimator, according to at least one embodiment of the invention, is manufactured by at least:

providing a number of collimator elements, each of the collimator elements being manufactured by at least applying a lithographic coating layer, exposing the lithographic coating layer in exposure regions corresponding to a structure of the collimator element, the structure of the collimator element being aligned on a common focus, developing the lithographic coating layer to provide a pre-structure of the collimator element;

applying an X-ray absorbing layer via cathode sputtering, and removing at least the X-ray absorbing layer from regions of the pre-structure; and joining the number of collimator elements together, to form the scattered-radiation collimator.

A radiation detector, according to at least one embodiment of the invention, comprises the scattered-radiation collimator of at least one embodiment.

A CT device, according to at least one embodiment, comprises the radiation detector of at least one embodiment.

BRIEF DESCRIPTION OF THE DRAWINGS

The invention will be explained again in more detail below by way of the attached figures and with reference to example embodiments. Here, like components are provided with identical reference numerals in the different figures. As a rule, the figures are not to scale. In the figures.

DETAILED DESCRIPTION OF THE EXAMPLE EMBODIMENTS

Figure 1:
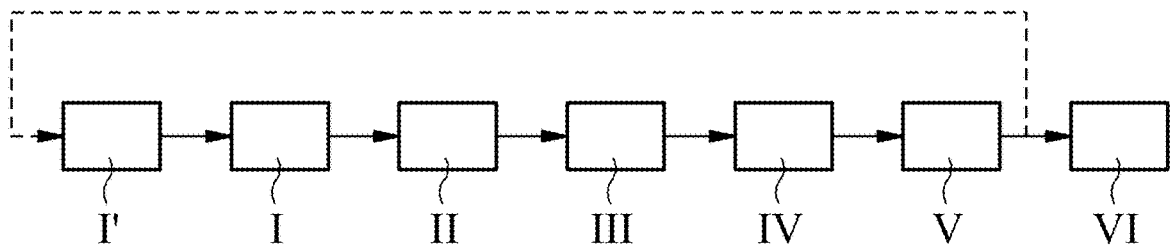
FIG. 1 shows a schematic block diagram of an example embodiment of a method according to the invention for manufacturing a collimator element.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

A method of at least one embodiment, for manufacturing a collimator element, includes at least: in one step, a lithographic coating layer which is at least 0.5 mm thick is applied. In a further step, the lithographic coating layer is exposed in exposure regions that correspond to a structure of the collimator element. Here, the structure of the collimator element is aligned on a common focus. Then, the lithographic coating layer is developed to give a pre-structure of a collimator element. In a still further step, an X-ray absorbing layer is applied via cathode sputtering. In a further step, at least the X-ray absorbing layer is removed from regions of the pre-structure.

The term "collimator element" is understood to mean a constituent part or a component of a scattered-radiation collimator. It forms at least a portion of the scattered-radiation collimator and is already in the form of a grid shape, as will be explained in more detail below. The term "grid" is understood in the context of embodiments of the invention to mean an arrangement comprising a first plurality of substantially mutually parallel grid walls which are crossed by a second plurality of likewise substantially mutually parallel grid walls that are transverse, preferably perpendicular, thereto in a common plane. In this arrangement, grid shafts ("shafts" for short) are formed between the grid walls. Here, the term "substantially" means that the walls are only almost parallel. When observed in more detail, however, they are all inclined slightly toward one another so that they are aligned on the focus. In other words, they all converge radially toward the focus. In this case, the almost parallel walls are inclined for example by less than 1° or below 1°.

The substrate may in principle comprise any desired substances whereof the surface is in particular smooth and planar. That is to say, the surface of the substrate has overall a height difference of at most a few micrometers. The substrate may for example be made from aluminum, glass, silicon, silicon dioxide or similar.

Preferably, in a preparatory step, a sacrificial coating layer that is for example a few tens of nanometers thick is applied to the substrate, for example by spin coating. The term "spin coating" is generally understood to mean a method for applying thin uniform layers by rotation. Here, first a desired quantity of a solution—that is to say a coating material dissolved in a solvent—is applied to the center of the substrate. Depending on the desired thickness of the coat and the solution used, the acceleration, speed of rotation and duration are set at a spin coating device, and a corresponding spin procedure is performed. During this, the solution is distributed evenly over the substrate surface. Typically, the solutions used are polymer solutions, wherein the molar mass and the distribution of the solution also influence the coating thickness.

In order to obtain a solid coating, it is necessary to remove the solvent. Some of the solvent already evaporates during the spin procedure. This may be promoted for example by simultaneous or subsequent heating (tempering, soft and/or hard baking, and a combination thereof), for example for 60 seconds at 200° C. As the sacrificial coating layer there may be used for example Omnicoat™.

A lithographic coating is applied to the sacrificial coating layer, for example via spin coating as described above, via a metering method or similar (e.g. via spraying, nozzles or the like). The lithographic coating is preferably a negative lithographic coating, or a negative photoresist. For example, SU-8 or nLOF are suitable as the lithographic coating.

The applied coating layers—that is to say the lithographic coating layer and the sacrificial coating layer (also called the coating system below)—are exposed by intensive UV light through a grid mask or exposure mask. That is to say that the coating system is subjected to electromagnetic radiation having a wavelength in the range of from 300 nm to 400 nm, preferably hard UV light with a wavelength of less than 350 nm. Here, the dimensions of the grid mask already correspond substantially to the grid structure of the collimator element to be produced. Here, the term "substantially" means that the effects of diffraction may be taken into account in the dimensions of the grid mask. Because of the high levels of thickness according to the invention of the lithographic coating layer, the coating layers are subjected to the UV light for an exposure time—that is to say the duration of the exposure—of more than 40 s, preferably approximately 60 s.

The lithographic coating layer is then developed. That is to say that, in the case of a negative lithographic coating, the unexposed regions are dissolved away using a solvent such as MR-Dev 600 (applied for 30 min with stirring). That is to say that in the case of a negative lithographic coating the exposed regions are made insoluble by photo-polymerization and remain on the substrate (in the case of a positive lithographic coating this is reversed, that is to say that the exposed regions become soluble). Thus, the fact that the exposed regions "correspond" to the structure of the collimator element means that they take a form that is substantially identical or complementary to the structure of the collimator element. The sacrificial coating layer is then removed by an O2 plasma (for 30 sec). This produces a pre-structure that takes a negative or complementary form to the collimator element to be produced. Consequently, in the following it serves so to speak as a template or "casting mold" for the grid that is to be produced, and already has the dimensions thereof.

The X-ray absorbing layer is applied to the pre-structure, or introduced between the pre-structure, via cathode sputtering. This term is used to describe in general a procedure in which atoms from a solid body (target) are isolated by bombardment with energy-rich ions (such as noble gas ions), and enter the gas phase. Known sputtering methods are for example ion beam sputtering, RF sputtering, DC sputtering, magnetron sputtering, reactive sputtering or similar. For this, the substrate with the pre-structure is brought close to the target so that the atoms ejected from the target can condense onto it. So that the target atoms reach the substrate with the pre-structure, cathode sputtering takes place in a vacuum. In this arrangement, the target and the X-ray absorbing layer to be produced may in principle include any material that absorbs X-rays to a pronounced extent, so for example tantalum, tungsten or similar.

The focus on which the collimator element to be manufactured is aligned is in particular a focus point. Thus, the dimension of the focus is negligibly small. The focus here corresponds to a notional focus of a radiation source for which the collimator element is manufactured, and the alignment corresponds to the radiation geometry in which the collimator element is to be used. In operation, direct radiation therefrom passes through the collimator element unhindered because of the alignment of the structure or the grid walls, while scattered radiation is suppressed.

Finally, the lithographic coating layer and where appropriate also the sacrificial coating layer are removed by wet-chemical means. For this purpose, for example the lithographic coating may be dissolved in an appropriately aggressive solvent such as TMAH (tetramethylammonium hydroxide), NMP (N-methyl-2-pyrrolidone) or acetone. For dissolving the sacrificial coating layer, a so-called stripper such as MF319 or MFCD26 is used. The lithographic coating layer and/or the sacrificial coating layer are dissolved where appropriate with stirring or with the assistance of ultrasound. The coating layers are lifted off from their side walls (edges). Thereafter, the X-ray absorbing layer only remains in the regions in which it is in direct contact with the substrate.

Here, lithographic coatings that enable a large layer height to be produced in one lithographic step are preferably used.

This on the one hand avoids performing a multiplicity of lithographic steps. On the other hand, it is no longer necessary to stack and glue a plurality of grid layers to one another. Rather, with the aid of the method according to the invention, a collimator or grid element is applied to the substrate in one piece or a single part, additively in one step or a few repetitions of the method, by cathode sputtering. This advantageously gives a manufacturing procedure that is more favorable and more efficient in terms of time, and smaller tolerances. As already mentioned in the introduction, it is specifically the tolerances of the grid walls that form an essential criterion in manufacturing a collimator element that is suitable for relatively small pixels. This is made possible by at least one embodiment of the invention.

In principle, the above-mentioned method of at least one embodiment could also be performed with a positive lithographic coating without making substantial changes. The elements required for this, for putting the shafts in shadow, could be connected to one another for example by thin supporting struts. These would on the one hand partly put in shadow the regions of the grid walls that are to be exposed, and on the other disadvantageously result in a more fragile exposure mask. By contrast, a grid mask for negative lithographic coating, by which the shafts are exposed and the grid walls put in shadow, is substantially simpler to make.

A collimator element is manufactured by a method according to at least one embodiment of the invention.

A method of at least one embodiment, for manufacturing a scattered-radiation collimator, includes at least the following. In one step, a number of collimator elements according to the invention are provided. In a further step, the collimator elements are joined together to form a scattered-radiation collimator. Here, "a number" means one or more. In principle, it would therefore be possible within the context of the invention to make a scattered-radiation collimator having only one collimator element. Because of the shape, in the manner of a circle chord, of the radiation detectors in CT devices, however, it is frequently more favorable and simpler to make the scattered-radiation collimator out of a plurality of collimator elements. When these are joined together, preferably each collimator element is aligned on the focus. Joining together may for example be performed form-fittingly and/or force-fittingly and/or via gluing, welding, soldering or similar types of connection. The scattered-radiation collimator mentioned in the introduction accordingly includes a number of collimator elements according to the invention and is manufactured in particular according to the method according to the invention that is described above.

The radiation detector of at least one embodiment includes a scattered-radiation collimator according to at least one embodiment of the invention. The radiation detector may take the form of a CT, PET or SPECT detector. In particular, it is a photon-counting and where appropriate also energy-resolved X-ray detector. In this case, a grid shaft is associated with each pixel of the radiation detector. That is to say that the grid shaft is positioned in relation to the pixel such that direct (not scattered) radiation falls on the pixel through the grid shaft.

The radiation detector that is described above may in principle be a constituent part of any desired X-ray device, such as a radiography device, an angiography device or in particular a CT device. The CT device of at least one embodiment includes a radiation detector according to at least one embodiment of the invention. The fundamental functioning of a radiation detector and of a CT device is known to those skilled in the art, so no further explanations in this regard will be given here.

New radiation detectors and/or CT devices already having the collimator elements and/or scattered-radiation collimators according to at least one embodiment of the invention may thus be made. Advantageously, however, already existing radiation detectors or CT devices may be retrofitted with the collimator elements according to at least one embodiment of the invention and/or scattered-radiation collimators according to at least one embodiment of the invention.

According to at least one embodiment of the invention, a scattered-radiation collimator according to at least one embodiment of the invention is used to absorb scattered radiation before the scattered radiation falls on a radiation detector.

Further particularly advantageous embodiments and developments of the invention become apparent from the claims and the description below, wherein the independent claims of one category of claim may also be developed in a manner analogous to the dependent claims of another category of claim and the description thereof, and in particular individual features of different example embodiments or variants may also be combined to form new example embodiments or variants.

The exposed regions are preferably aligned on the focus via a grid arrangement having a number of grid masks. Here, the grid masks together form apertures for the light that are aligned on the focus. That is to say that the grid masks preferably have different structures, wherein the structure of the grid mask closer to the light source preferably takes a finer form and the structure of the grid mask closer to the substrate preferably takes a coarser form in relation to one another. Because the light for polymerization of the lithographic coatings can only penetrate through the apertures formed by both grid masks, only the regions of the lithographic coating that are located in a line continuing beyond these apertures are polymerized. Thus, the exposure may be performed for example using an area light source preferably of homogeneous radiance. Likewise, using the grid arrangement described above, exposure using a point light source is possible, as will be described below.

As an alternative or in addition, preferably at least one grid mask is exposed using a point light source. The point light source is in this case preferably arranged at the position of the focus, or the grid mask is modified accordingly (e.g. by a suitable thickness, a spacer from the coating system and/or the like). This replicates the geometry of the radiation with which the collimator element is to be utilized later. Thus, by way of the point light source and the exposure through at least one grid mask, it is already ensured that the regions of the lithographic coating to be polymerized are aligned on the focus. In order for example to obtain sharper edges, exposure using a point light source may be combined with the grid arrangement described above.

The point light source may in this case take the form for example of a UV laser. In addition or as an alternative, in the case of a conventional light source (not a laser) the point characteristic of the light source may be improved or created using suitable optical elements. Here, optical elements that are preferably used are pinhole diaphragms, optical gratings or a combined arrangement thereof.

Preferably, a lithographic coating is used by which comparatively thick layers can be obtained. This advantageously makes it possible already to obtain the desired grid height in one or a few lithographic steps, as will be described in more detail below.

SU-8 is for example available in different viscosities, which are controlled by the proportion of solvent in the lithographic coating.

Negative coatings with which a greater layer thickness of at least 1 mm can be obtained are for example SU-8 1000 SU-8 3050. They are thus preferably used in the context of the method according to at least one embodiment of the invention.

Sealing the lithographic coating layer or the sacrificial coating layer by the X-ray absorbing layer is to be avoided, since as a result the solvent can no longer act on the coating layers and so lift-off would be prevented. In order to counter sealing, the thickness of the coating layers is preferably selected to be greater than that of the X-ray absorbing layer. The ratio of the thicknesses between the layer coatings and the X-ray absorbing layer is at least 1:1. For this reason, the lithographic coating layer is preferably applied in a layer at least 0.5 mm, particularly preferably at least 1 mm, very particularly preferably 2 mm, and even more preferably 3 mm.

In principle, the thinner the walls of the collimator element the more the DQE (detective quantum efficiency) will increase, since in this way a smaller detection surface area of the radiation detector is screened. Thus, the grid mask preferably has shadowing regions whereof the shadowing width is less than or equal to 100 µm, particularly preferably less than 50 µm, very particularly preferably less than 20 µm and most preferably approximately 10 µm. Accordingly, a collimator element according to the invention, in particular a collimator element made according to the method according to at least one embodiment of the invention, preferably has grid walls whereof the wall thickness is less than or equal to 100 µm, particularly preferably less than 50 µm, very particularly preferably less than 20 µm and most preferably approximately 10 µm.

Overall, using the method according to at least one embodiment of the invention the previously conventional tolerances of approximately 20 µm for thickness and alignment of the grid walls may advantageously be significantly reduced.

In order to adapt to currently conventional or indeed future generations of pixels of a radiation detector, the grid mask preferably has shadowing regions that are spaced by an exposure width of at most 400 µm, particularly preferably at most 300 µm, very particularly preferably at most 200 µm, even more preferably at most 100 µm. Accordingly, a collimator element according to at least one embodiment of the invention, in particular a collimator element made according to the method according to the invention, has grid walls that are spaced by a shaft width of preferably at most 400 µm, particularly preferably at most 300 µm, very particularly preferably at most 200 µm, even more preferably at most 100 µm.

In order to achieve the best absorption possible, the X-ray absorbing layer preferably includes tungsten as a constituent part. Particularly preferably, it is made of pure, that is to say as far as possible 100% tungsten, since this absorbs the radiation even better. Accordingly, a collimator element according to at least one embodiment of the invention is particularly preferably made of pure tungsten.

In order as a whole to obtain a sufficient height of the collimator element, in a method according to at least one embodiment of the invention the steps I to VI are preferably repeated, wherein where appropriate the exposure regions and the grid masks used are adapted accordingly. As a result, advantageously the height of the grid may be adapted within the context of at least one embodiment of the invention in dependence on the size of the grid structure or the grid shafts.

Preferably, during a repetition exposure regions that are offset from the previous exposure regions are exposed, with the result that a stepped structure of the collimator element, aligned on the common focus, is formed. This can be achieved relatively simply, for example via a corresponding set or plurality of grid masks and exposure over an area, preferably homogenously over the area. Here, before a subsequent repetition of the method steps a grid mask of a previously generated stage is replaced by a grid mask for the next stage, which follows the stepped arrangement to be manufactured in accordance with the structure.

Here, scattered-radiation collimation depends in particular on the so-called shaft ratio, or the shaft size inverse thereto. The shaft size specifies the ratio of the spacing between two mutually opposite shaft walls to the shaft height, or the height of the collimator element. Thus, the smaller the spacing between the opposite shaft walls, with the same shaft ratio the smaller the height of the collimator element can be too.

The demands made of scattered-radiation collimation are particularly high in the case of dual- and multi-energy CT applications. Here, for example a shaft ratio of 1:20 is needed. It is thus possible with a defined pixel size for the height of the collimator element that is to be manufactured to be determined.

Here, the small tolerances achievable according to at least one embodiment of the invention which have been described above enable good collimation with small pixels and at the same time a negligible effect on the detective quantum efficiency. The relatively large heights of the collimator elements that are achievable according to at least one embodiment of the invention and which have been described above enable sufficient collimation of the incident radiation even with relatively large pixels. Using the method according to the invention, it is thus possible to manufacture collimator elements for a broad range of applications.

Preferably, the substrate is removed from the collimator element. This may be performed for example via suitable dry-chemical and/or wet-chemical methods. In dry-chemical terms, the substrate could for example be removed from the collimator element by grinding. More efficiently, however, the substrate is particularly preferably separated or removed from the collimator element by wet-chemical devices/methods, via a suitable solvent for the substrate, such as hydrofluoric acid (HF).

FIG. 1 shows by way of example a schematic block diagram of the course of a manufacturing method according to an embodiment of the invention of a collimator element 20 according to the invention. FIG. 1 will be explained in more detail below by way of FIG. 2 to FIG. 7.

In a preparatory step I', a sacrificial coating layer 21 of Omnicoat™ is applied via spin coating. For this purpose, a quantity of 50 µl/2.25 $cm^2$ of Omnicoat™ is metered onto a planar substrate 22 for example of silicon oxide. Then, the substrate with the applied Omnicoat™ is rotated, first for 10 seconds at 500 rpm at 500 rpm, followed by 50 sec at 300 rpm. Thereafter, the applied Omnicoat™ is heated to 160° C. for 30 sec for the purpose of curing. The above procedure is repeated once. Finally, 50 µl/2.25 $cm^2$ of Omnicoat™ is again metered on, and the system is rotated for 10 sec at 500 rpm and then for 50 sec at 300 rpm. This is followed by heating to 200° C. for 60 sec in order to cure the entire sacrificial coating layer.

In a further step I, a lithographic coating layer 23 of SU-8 3050 is applied to the cured sacrificial coating layer 21 via spin coating. For this, in a first sub-procedure 0.2 ml/2.25 cm² of SU-8 3050 is metered onto the sacrificial coating layer 21. The substrate is then rotated for 20 sec at 500 rpm, followed by 20 sec at 1 000 rpm, in order to distribute the applied lithographic coating evenly. The first sub-procedure is repeated twice. Then, in a second sub-procedure, another 0.2 ml/2.25 cm² of SU-8 3050 is metered on, and then the substrate with the applied layers is rotated for 30 sec at 500 rpm. The second sub-procedure is repeated once. For curing, the substrate with the applied layers is first baked for 60 sec at 65° C., and then heated to 95° C. over a period of 60 sec and baked for 6 h.

Figure 2:
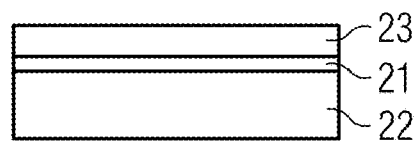
FIG. 2 shows a schematic sectional view of a product after manufacturing steps I) and II) of the method explained by way of FIG. 1.
Figure 3:
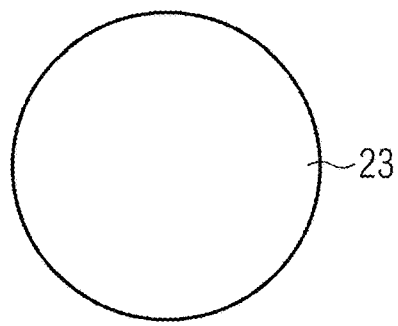
FIG. 3 shows a plan view of the product from FIG. 2.
Figure 4:
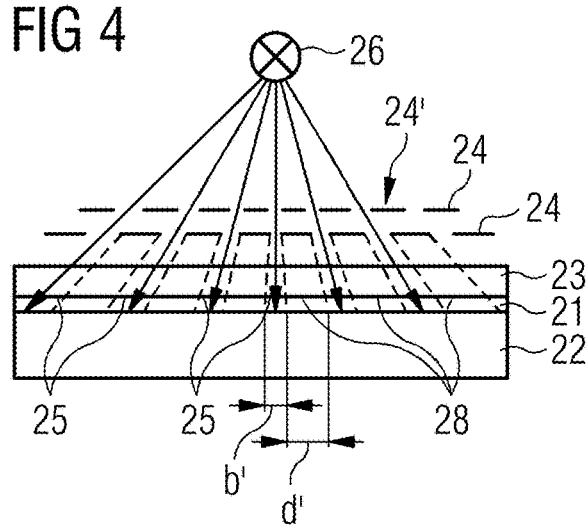
FIG. 4 shows a schematic sectional view during manufacturing step III) and a schematic sectional view after manufacturing step IV) of the method explained by way of FIG. 1.

The result or the product of steps I' and I is illustrated by way of example in FIG. 2 in a sectional view and in FIG. 3 in a plan view. FIG. 2 shows the structure of the layers. The substrate 22, made of silicon, may in principle have any desired thickness. In this case, by way of example it is 0.525 mm thick. This is followed by the sacrificial coating layer 21, which is for example 0.06 µm thick, and finally the lithographic coating layer 23, which is for example 500 µm thick. The plan view in FIG. 3 merely shows a smooth lithographic coating layer 23.

In a further step II (see FIG. 4), the lithographic coating layer 23 and the sacrificial coating layer 21 are irradiated by an ultraviolet point light source 26, through a grid mask arrangement 24'. The grid mask arrangement 24' includes two grid masks 24. The grid masks 24 are in this case structured and arranged such that they form exposure regions 25 having an exposure width b', through which the UV radiation (indicated schematically here by arrows) passes. Further, the grid mask arrangement 24' has shadowing regions 28 having a shadow width d' that screen the coating layers 21, 23 from the UV radiation. The exposure regions 25 and shadowing regions 28, which represent a continuation of the grid mask arrangement 24', here correspond substantially—that is to say, not taking into account the influence of diffraction effects—in their shape and dimensions to the collimator element 20 that is to be manufactured. During the irradiation, the lithographic coating layer 23 is polymerized, and cures in the exposure regions 25.

Although the UV light source is illustrated and described here as a light point source 26, the method according to the invention using the grid arrangement 24' may also be performed with an area light source, for example in order to achieve more homogeneous polymerization. In this way, in addition to the point light source 26 there may also be used for example another point light, a planar lamp or another suitable UV light source.

In order to cure the polymerized regions of the lithographic coating layer 23 further, it is heated at 95° C. for 6 min in a post-exposure bake.

In a further method step III, the lithographic coating layer 23 is developed by putting the substrate 22 with the coating layers into a developer bath, for example in MR-Dev 600 for 30 min, with stirring and then heating it at 130° C. for 60 min. During this, the unexposed and hence unpolymerized regions of the lithographic coating layer 23 are dissolved away. The sacrificial coating layer 21 underneath is then removed by the action of an O2 plasma on it for 30 seconds. The developed lithographic coating layer 23' and the sacrificial coating layer 21' now together have a pre-structure 27 that is complementary to the collimator element 20 to be manufactured. Baking of the substrate having the pre-structure 27 is then completed, for 60 min at 130° C.

Figure 5:
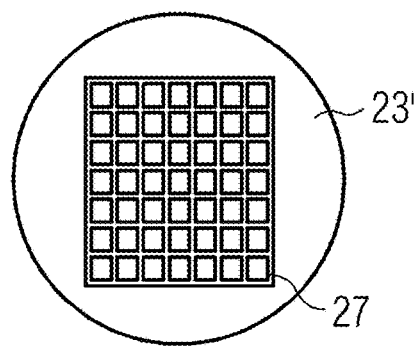
FIG. 5 shows a plan view of the product from FIG. 4.
Figure 6:
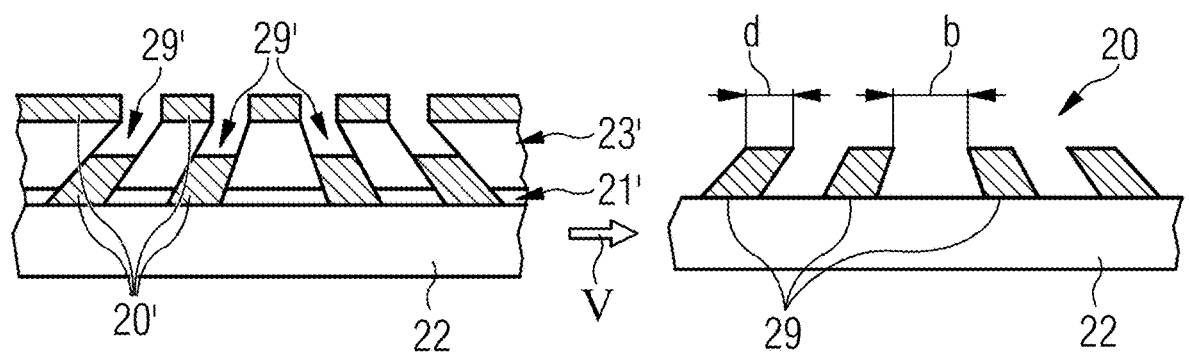
FIG. 6 shows a schematic sectional view during manufacturing step V) and a schematic sectional view after manufacturing step VI) of the method explained by way of FIG. 1.

The grid-shaped pre-structure 27 is illustrated in plan view in FIG. 5. The pre-structure 27 is surrounded by a planar surface of the developed lithographic coating layer 23'. The pre-structure 27 has a first number of mutually substantially parallel channels 29', and a second number of likewise mutually substantially parallel channels 29' perpendicular thereto.

In a further step IV (see FIG. 6), a pure tungsten layer 20' that is for example 370 µm thick is deposited evenly on the substrate 22 and the developed coating layers 21', 23' by cathode sputtering. The tungsten layer 20' condenses, or is deposited, in the channels 29' of the pre-structure 27 and on the developed lithographic coating layer 23'. Because of the difference in height between the channels 29' and the upper side of the developed lithographic coating layer 23', there is no sealing of the developed lithographic coating layer 23' and the sacrificial coating layer 21'.

In the following step V, the substrate 22 with the developed coating layers 21', 23' and the tungsten layer 20' is treated with a strong solvent such as NMP, where appropriate with stirring or ultrasound. As a result the lithographic coating layer 23' is removed. The sacrificial coating layer 21' is removed by a so-called stripper such as MFCD26 or MF319, where appropriate with stirring or ultrasound. The tungsten layer 20' only remains in the regions in which it has been deposited directly on the substrate 22, within the pre-structure 27, and so forms the collimator element 20.

Figure 7:
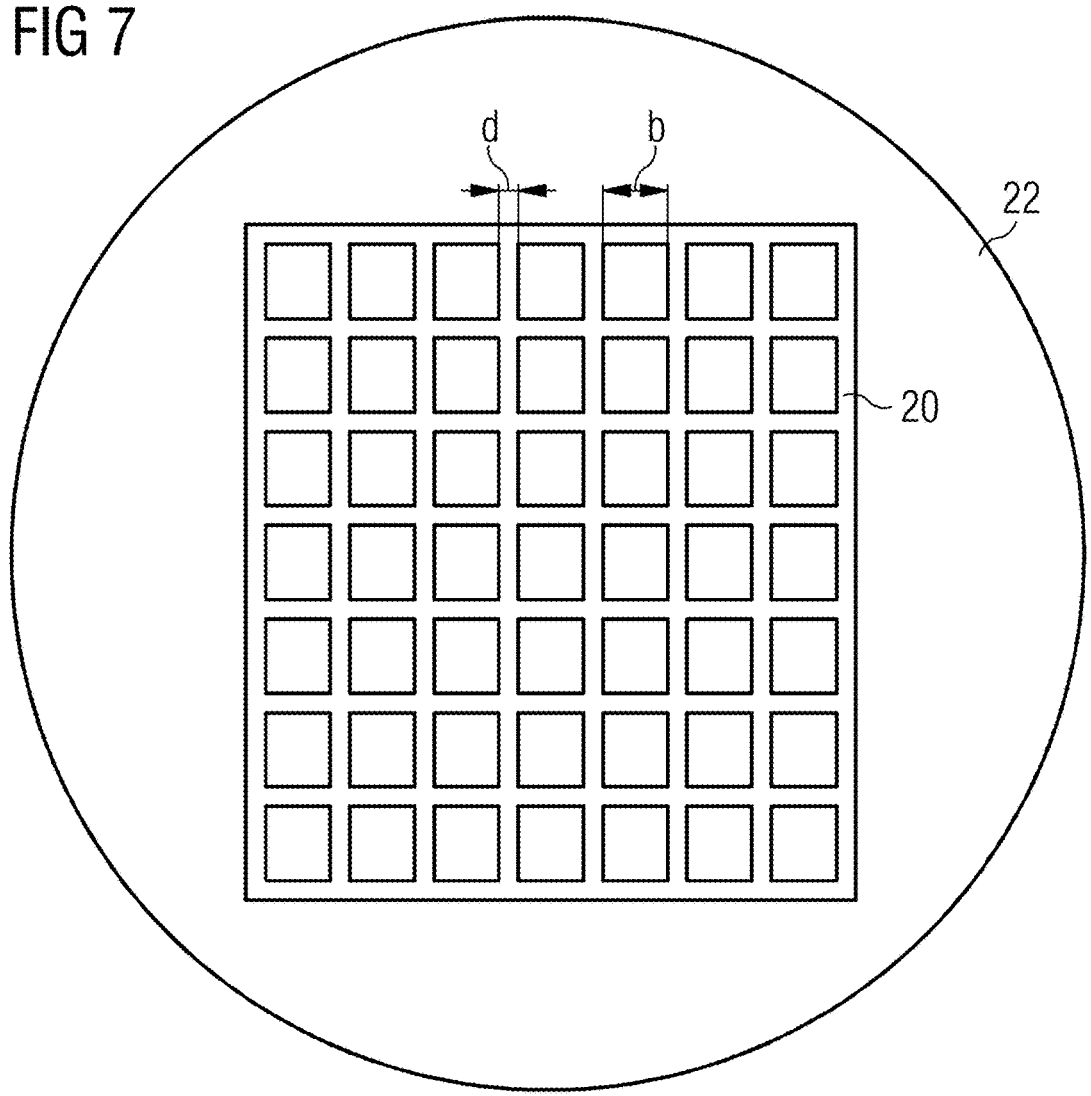
FIG. 7 shows a plan view of the product from FIG. 6, namely an example embodiment of a collimator element according to the invention.

A collimator element 20 according to the invention is illustrated by way of example in a plan view in FIG. 7. In this illustration, it is shown still arranged on the substrate 22 and, corresponding to the pre-structure 27, has a first number of mutually substantially parallel grid walls 29 and a second number of mutually substantially parallel grid walls 29 perpendicular thereto. The grid walls 29 have a wall thickness d of for example 10 µm and are each arranged at a spacing from a shaft width b of for example 200 µm. This accordingly produces a shaft ratio of 1:20, also suitable for dual- and multi-energy applications.

Figure 8:
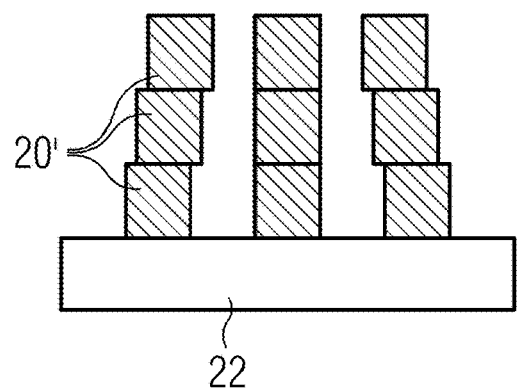
FIG. 8 shows a rough schematic sectional view of a further example embodiment of a collimator element according to the invention.

FIG. 8 illustrates, in a rough schematic sectional view, a further example embodiment of a collimator element according to the invention on the substrate 22. Three tungsten layers 20' have been applied to the substrate 22, in a repetition of the method steps I to V described above. In each of these repetitions, different grid masks 24 are used, in order to generate a corresponding structure of the respective tungsten layer 20'. The overall structure of the collimator element 20 formed by the tungsten layers 20' is in this case, and according to the invention, aligned on a focus.

As mentioned above, the figures are schematic and not to scale. In particular, the angles illustrated in FIG. 4, FIG. 6 and FIG. 8 between the light beams and the resulting angles between the exposure regions 25 and the grid walls 29 are greatly exaggerated for the sake of illustration. In a real arrangement in an X-ray system, they are produced substantially from the spacing between the opposite grid walls 29, which frame a detector pixel, and the spacing between the detector surface for focusing the X-ray source. The angle between two opposite grid walls 29 is in each case preferably less than 1°.

In a concluding method step VI, the substrate 22 is removed from the collimator element 20. This is preferably done by a wet-chemical method, for example via hydrofluoric acid (HF). The hydrofluoric acid dissolves the substrate 22 of silicon dioxide but does not attack the collimator element 20 made of tungsten. The collimator element 20 according to the invention has substantially already been described with reference to FIG. 7.

In order to manufacture a scattered-radiation collimator according to the invention, a number of the collimator elements according to the invention, manufactured in the manner just described, are provided and joined together for example by gluing such that they are arranged for example in a segment of part of a circle.

Figure 9:
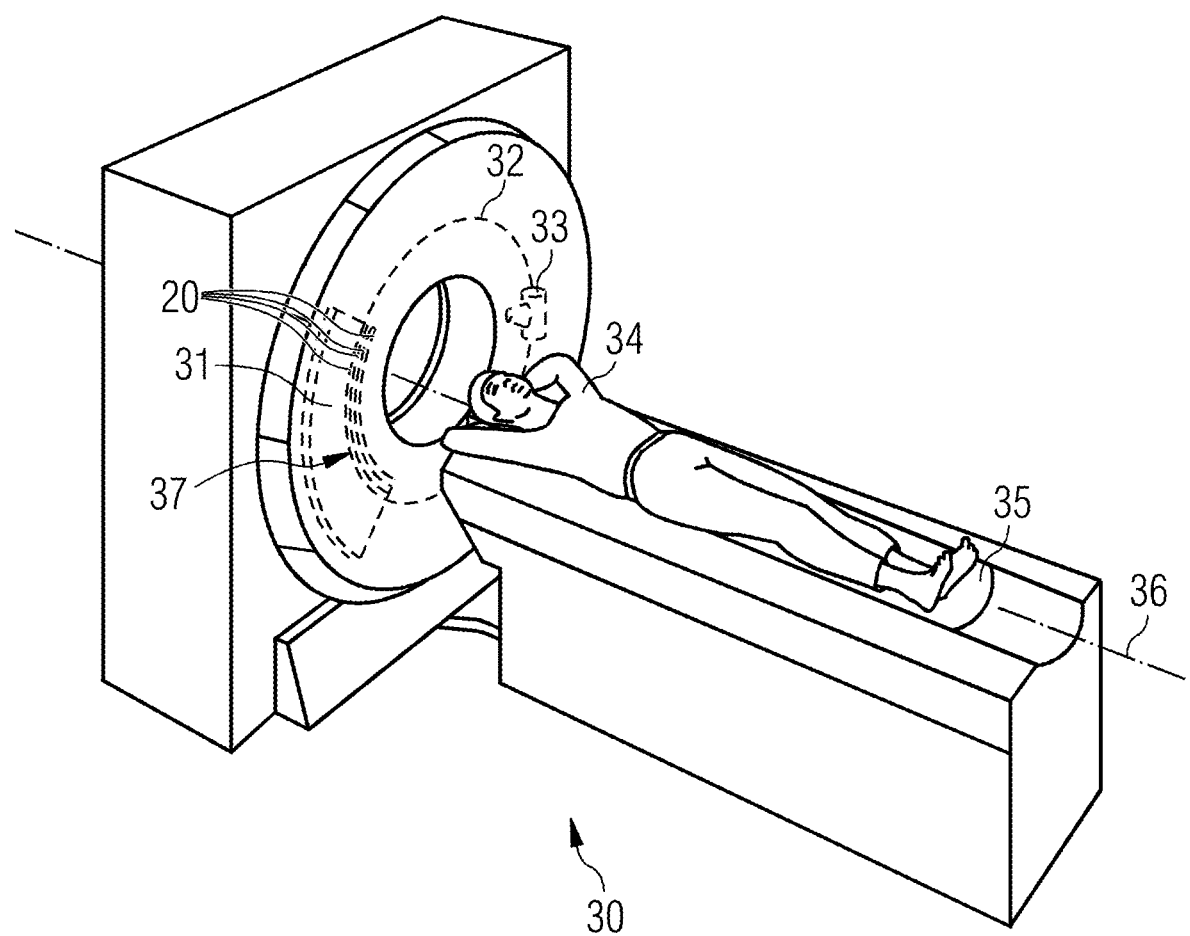
FIG. 9 shows a perspective view of an example embodiment of a CT device according to the invention.

FIG. 9 shows by way of example and in a rough schematic form a computed tomography device or CT device 30 according to the invention. The computed tomography device 30 includes a patient table 35, for supporting a patient 34 as the object undergoing investigation. The patient table 35 can be moved into the measuring zone along a system axis 36, and by so doing the patient 34 can be positioned in the measuring zone. The computed tomography device 30 further includes a gantry 32 having a source radiation detector arrangement 33, 31 mounted such that it can rotate about the system axis 36. The source radiation detector arrangement 33, 31 has an X-ray source 33 and an example embodiment of a radiation detector 31 according to the invention, and these are aligned in opposition to one another such that during operation X-rays emitted from the focus of the X-ray source 33 fall on the radiation detector 31. On the side of the radiation detector 31 pointing to the X-ray source 33 there is arranged an example embodiment of a scattered-radiation collimator 37 according to the invention. The scattered-radiation collimator 37 has a number of collimator elements 20 according to the invention, which are arranged on the inner segment—that is to say on the side pointing toward the system axis 36—of a part circle of the radiation detector 31.

The scattered-radiation collimator 37 collimates the X-rays once they have passed through the patient. As a result, the effects of scattered radiation during acquisition are largely avoided. For each projection, the radiation detector 31 generates a set of projection data. This projection data is then processed further, to produce a resulting image.

The use of a computed tomography device 30 of this kind for 3D image reconstruction is known. For capturing an image of an object undergoing investigation (region of interest), as the source radiation detector arrangement 33, 31 rotates projection data is detected from a multiplicity of different projection directions. In the case of helical scanning, during rotation of the source radiation detector arrangement 33, 31, for example at the same time the patient table 35 is moved continuously in the direction of the system axis 36. With this type of scanning, the X-ray source 33 and the radiation detector 31 thus move around the patient 34 over a helical path. The precise construction and the concrete mode of operation of a CT device 30 of this kind are known to those skilled in the art and so are not explained in detail here.

Lithography and cathode sputtering methods are fundamentally established procedures that allow manufacture that is highly precise and at the same time low in cost. Using the methods according to the invention, it is thus possible to manufacture lower-cost collimator elements and scattered-radiation collimators, which moreover meet higher demands of the tolerances of manufacture. As a result, post-treatment is also largely avoided.

Finally, it should also be pointed again that the devices described in detail above are merely example embodiments, which may be modified by those skilled in the art in the greatest variety of ways without departing from the scope of the invention. Furthermore, the use of the indefinite articles "a" and "an" does not rule out the possibility that the features concerned may also be present a plurality of times. Likewise, the terms "device" and "element" do not rule out the possibility that the component concerned comprises a plurality of cooperating partial components, which where appropriate may also be spatially separated from one another.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for manufacturing a collimator element, comprising at least the following steps:
   applying a lithographic coating layer;
   exposing the lithographic coating layer in exposure regions corresponding to a structure of the collimator element, the structure of the collimator element being aligned on a common focus;
   developing the lithographic coating layer to provide a pre-structure of the collimator element;
   applying an X-ray absorbing layer via cathode sputtering; and
   removing at least the X-ray absorbing layer from regions of the pre-structure, wherein during a repetition of the steps of the method, exposure regions offset from at least one previous exposure region are exposed, resulting in formation of a stepped structure of the collimator element, aligned on a common focus.

2. The method of claim 1, wherein the exposed regions are aligned on the common focus via a grid arrangement including a number of grid masks.

3. The method of claim 2, wherein at least one grid mask of the grid arrangement is exposed using a point light.

4. The method of claim 1, wherein the exposed regions are aligned on the common focus via a grid mask, the grid mask including shadowing regions including a shadowing width of less than 20 µm.

5. The method of claim 1, wherein the exposed regions are aligned on the common focus via a grid mask, the grid mask including shadowing regions, spaced by an exposure width of at most 400 µm.

6. The method of claim 1, wherein the X-ray absorbing layer includes tungsten as a constituent part.

7. The method of claim 1, wherein the X-ray absorbing layer is made of pure tungsten.

8. The method of claim 1, wherein the exposed regions are aligned on the common focus via a grid mask, the grid mask including shadowing regions including a shadowing width of less than 10 µm.

9. The method of claim 1, wherein the exposed regions are aligned on the common focus via a grid mask, the grid mask including shadowing regions, spaced by an exposure width of at most 100 µm.

10. A collimator element, manufactured by at least:
applying a lithographic coating layer;
exposing the lithographic coating layer in exposure regions corresponding to a structure of the collimator element, the structure of the collimator element being aligned on a common focus;
developing the lithographic coating layer to provide a pre-structure of the collimator element;
applying an X-ray absorbing layer via cathode sputtering; and
removing at least the X-ray absorbing layer from regions of the pre-structure, wherein during a repetition of the applying of the lithographic coating layer, exposing, developing, applying the X-ray absorbing layer, and removing, exposure regions offset from at least one previous exposure region are exposed, resulting in formation of a stepped structure of the collimator element, aligned on a common focus.

11. The collimator element of claim 10, including a number of X-ray absorbing layers structured via lithography and, aligned on a common focus, and formed from pure tungsten.

12. The collimator element of claim 10, including grid walls, a wall thickness of the grid walls being less than or equal to 100 µm.

13. The collimator element of claim 12, wherein the grid walls are spaced by a shaft width of at most 400 µm.

14. A method for manufacturing a scattered-radiation collimator, comprising:
providing a number of collimator elements, each of the collimator elements being manufactured by at least
applying a lithographic coating layer,
exposing the lithographic coating layer in exposure regions corresponding to a structure of the collimator element, the structure of the collimator element being aligned on a common focus,
developing the lithographic coating layer to provide a pre-structure of the collimator element;
applying an X-ray absorbing layer via cathode sputtering, and
removing at least the X-ray absorbing layer from regions of the pre-structure, wherein during a repetition of the applying of the lithographic coating layer, exposing, developing, applying the X-ray absorbing layer, and removing, exposure regions offset from at least one previous exposure region are exposed, resulting in formation of a stepped structure of the collimator element, aligned on a common focus; and
joining the number of collimator elements together, to form the scattered-radiation collimator.

15. The scattered-radiation collimator, including the number of collimator elements joined, of claim 14.

16. A radiation detector, comprising the scattered-radiation collimator of claim 15.

17. A CT device comprising the radiation detector of claim 16.

18. A scattered-radiation collimator, manufactured by at least:
providing a number of collimator elements, each of the collimator elements being manufactured by at least
applying a lithographic coating layer,
exposing the lithographic coating layer in exposure regions corresponding to a structure of the collimator element, the structure of the collimator element being aligned on a common focus,
developing the lithographic coating layer to provide a pre-structure of the collimator element;
applying an X-ray absorbing layer via cathode sputtering, and
removing at least the X-ray absorbing layer from regions of the pre-structure, wherein during a repetition of the applying of the lithographic coating layer, exposing, developing, applying the X-ray absorbing layer, and removing, exposure regions offset from at least one previous exposure region are exposed, resulting in formation of a stepped structure of the collimator element, aligned on a common focus; and
joining the number of collimator elements together, to form the scattered-radiation collimator.

19. The scattered-radiation collimator, including the number of collimator elements joined, of claim 18.

20. A radiation detector, comprising the scattered-radiation collimator of claim 19.

21. A CT device comprising the radiation detector of claim 20.

* * * * *